US006333316B1

(12) United States Patent
Daifotis et al.

(10) Patent No.: US 6,333,316 B1
(45) Date of Patent: *Dec. 25, 2001

(54) METHOD FOR INHIBITING BONE RESORPTION

(75) Inventors: Anastasia G. Daifotis, Westfield; Arthur C. Santora, II, Watchung; A. John Yates, Westfield, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/376,314

(22) Filed: Aug. 18, 1999

Related U.S. Application Data

(63) Continuation of application No. 09/134,214, filed on Aug. 14, 1998, which is a continuation of application No. PCT/US98/14796, filed on Jul. 17, 1998.
(60) Provisional application No. 60/053,535, filed on Jul. 23, 1997, and provisional application No. 60/053,351, filed on Jul. 22, 1997.

(51) Int. Cl.[7] ........................ A61K 31/66; A61K 31/415; A61K 31/385; A61K 31/34
(52) U.S. Cl. .......................... 514/108; 514/399; 514/439; 514/461; 514/395
(58) Field of Search .................................. 514/108, 399, 514/439, 461, 395

(56) References Cited

U.S. PATENT DOCUMENTS

| | | | |
|---|---|---|---|
| 4,425,339 | 1/1984 | Pitchford | 424/239 |
| 4,621,077 | 11/1986 | Rosini et al. | 514/108 |
| 4,761,406 | 8/1988 | Flora et al. | 514/86 |
| 4,812,304 | 3/1989 | Anderson et al. | 424/112 |
| 4,822,609 | 4/1989 | Flora | 424/112 |
| 4,927,814 | 5/1990 | Gall et al. | |
| 4,980,171 | 12/1990 | Fels et al. | 424/473 |
| 5,270,365 | 12/1993 | Gertz et al. | 514/108 |
| 5,358,941 | 10/1994 | Bechard et al. | |
| 5,366,965 | 11/1994 | Strein | 514/102 |
| 5,488,041 | 1/1996 | Barbier et al. | 514/108 |
| 5,583,122 | 12/1996 | Benedict et al. | |
| 5,616,560 | 4/1997 | Geddes et al. | 514/12 |
| 5,616,571 | 4/1997 | Daifotis et al. | |
| 5,622,721 | 4/1997 | Dansereau et al. | |
| 5,773,429 | 6/1998 | Fuisz | 514/102 |
| 5,780,455 | 7/1998 | Brenner et al. | 514/108 |
| 5,804,570 | 9/1998 | Santora, II et al. | |
| 5,853,759 | 12/1998 | Katdare et al. | |

FOREIGN PATENT DOCUMENTS

| | | |
|---|---|---|
| 0 274 158 | 7/1988 | (EP) . |
| 0 600 834 A1 | 6/1994 | (EP) . |
| WO 94/00129 | 1/1994 | (WO) . |
| WO 94/00130 | 1/1994 | (WO) . |
| WO 94/21242 | 9/1994 | (WO) . |
| WO 95/08331 | 3/1995 | (WO) . |
| WO 95/28145 | 10/1995 | (WO) . |
| WO 95/28936 | 11/1995 | (WO) . |
| WO 95/30421 | 11/1995 | (WO) . |
| WO 96/17616 | 6/1996 | (WO) . |

OTHER PUBLICATIONS

Singer et al., Advances in Endcrin. & Metab., vol. 6 (1995), pp. 259–288, "Bisphosphonates in the treatment of disorders of mineral metabolism".
Lieberman et al., N. Eng. J. of Medicine, vol. 333 (1995), pp. 1437–1443, Effect of oral alendronate on bone mineral density and the incidence of fractures in postmenopausal.
Bankhurst et al., Arthritis and Rheumatism, vol. 38, No. 9, Suppl. 1 (1995), S359, Three–year treatment with alendronate prevents fractures in women with postmenopausal.
de Vernejoul et al., Calcified Tissue Int'l, vol. 40 (1987), pp. 160–165, "Different schedules of administration of (3 amino–1–hydroxypropylidene)–1,1–bisphosphonate induce different changes . . .".
Lufkin et al., Osteoporosis Int'l. (1994), vol. 4, pp. 320–322, "Pamidronate: An unrecognized problem in gastrointestinal tolerability".
De Groen et al., N. England J. of Medicine, (1996), vol. 335, pp. 1016–1021, "Esophagitis associated with the use of alendronate".
Castell, (an editoral), N. England J. of Medicine (1996), vol. 335, pp. 1058–1059, "Pill esophagits—the case of alendronate".
Liberman et al., (correspondnece), N. England J. of Medicine (1996), vol. 335, pp. 1069–1070, "Esophagitis and alendronate".
Chestnut et al., Am. J. of Medicine, vol. 99, (1995), pp. 144–152, "Alendronate treatment of the postmenopausal osteoporotic woman . . .".
Cassidy et al., Digestive Diseases and Sciences, vol. 37 (1992), pp. 1206–1211, "Continuous versus intermittent acid exposure in production of esophagitis in feline model".
Mortensen et al., J. of Bone & Mineral Res., (1995) vol. 10, suppl. 1, p. s140, "Prevention of early postmenopausal bone loss by risedronate".
Melsen et al., Osteoporosis, Chapt. 60 (1996), pp. 1145–1158, "ADFR—The concept and its performance".
Thompson et al., J. of Bone & Min. Research, vol. 7 (1992), pp. 951–960, "The bisphosphonate, alendronate, prevents bone loss in ovariectomized baboons".
Balena et al., J. Clin. Invitest., vol. 92 (1993), pp. 2577–2586, "The effects of 2–year treatment with the aminobisphosphonate alendronate on bone metabolism, bone histomorphometry, and bone strength in ovariectomized nonhuman primates".

(List continued on next page.)

Primary Examiner—Theodore J. Criares
(74) Attorney, Agent, or Firm—Anthony D. Sabatelli; Melvin Winokur

(57) ABSTRACT

Disclosed are methods for inhibiting bone resorption in mammals while minimizing the occurrence of or potential for adverse gastrointestinal effects. Also disclosed are pharmaceutical compositions and kits for carrying out the therapeutic methods disclosed herein.

65 Claims, 8 Drawing Sheets

OTHER PUBLICATIONS

Peter et al., Digestive Diseases & Sciences, vol. 43 (1998), pp. 1009–1015, "Comparative study of potential for bisphosphonates to damage gastric mucosa of rats".

Peter et al., Digestive Diseases & Sciences, vol. 43 (1998), pp. 1998–2002, "Esophageal irritaton due to alendronate sodium tablets".

Filipponi et al., J. of Bone & Min. Research, vol. 10 (1995), pp. 697–703, "Cyclical clondronate is effective in preventing postmenopausal bone loss: A comparative study with transcutaneous hormone replacement therapy".

McClung et al., Bone, vol. 17 (1995), pp. 493S–496S, "Tiludronate therapy for Paget's disease of bone".

Seltenmeyer et al., Bone (NY), vol. 20, No. 4, Suppl., (1997) pp. 114S, "A comparison of the antiresorptive potency of various bisphosphonates in vivo with their inhibitory effect in vitro on squalene synthase and cellular sterol synthesis".

Adachi et al., Today's Therapeutic Trends, vol. 14, No. 1 (1996), pp. 13–24, "Osteoporosis—Its diagnosis, management and treatment with a new oral bisphosphonate agent, etidronate".

Bell et al., Endocrine, vol. 6(2) (1997), pp. 203–206, "Bisphosphonates in the Treatment of Osteoporosis".

Harris et al., J. of Clin. Endoc. & Metab., 76:1399–1406 (1993), "The effect of short term treatment with alendronate on vertebral density and biochemical markers of bone . . . ".

Lunar News, Apr. 1997, "Update: Bisphosphonate", pp. 30–32.

Gertz et al., Osteoporosis Int. (1993), Suppl. 3: S13–16, "Clinical pharmacology of alendronate sodium".

Gertz et al., Clin. Pharma. Ther. (1995), vol. 58, pp. 288–298, "Studies of the oral bioavailability of alendronate".

Khan et al., Bone, vol. 20 (1997), pp. 263–271, "Alendronate in the treatment of Paget's disease of bone".

Physician's Desk Reference, 51st ed. (1997), pp. 1703–1706, "Fosamax".

Gertz et al., J. of Bone & Min. Res., vol. 9 (1994), pp. 135–142, "Monitoring bone resorption in early postmenopausal women by an immunoassay for cross–linked collagen peptides in urine".

Fleisch, J. of Clin. Endoc. & Metab., vol. 76 (1993), pp. 1397–1398, "Editorial: Prospective use of bisphosphonates in osteoporosis".

Chestnut et al., Osteoporosis Int'l (1993), Suppl. 3: S17–19, "Short–term effect of alendronate of bone mass and bone remodeling in postmenopausal women".

Gertz et al., J. of Bone & Min. Res., vol. 6, Suppl. 1 (1991), Abstract No. 790, p. S281, "Oral bioavailability and dose proportionality of alendronate (aminohydroxybutylidene bisphosphonate) in postmenopausal women".

Mortensen et al., J. Bone & Min. Res., (1995) 10 (Supp. 1): S360, "Prevention of early postmenopausal bone loss by risendronate: A two year study".

Actonel™ (risedronate sodium tablets) package insert, dated Mar. 1998.

METHOD FOR INHIBITING BONE RESORPTION

CROSS-REFERENCE TO RELATED APPLICATIONS

This application is a continuation of U.S. application Ser. No. 09/134,214, filed Aug. 14, 1998, which is a continuation of PCT/US98/14796, filed Jul. 17, 1998, which claims the benefit of U.S. Provisional Application Ser. No. 60/053,535, filed Jul. 23, 1997 and U.S. Provisional Application Ser. No. 60/053,351, filed Jul. 22, 1997, the contents of all of the foregoing of which are hereby incorporated by reference in their entirety.

FIELD OF THE INVENTION

The present invention relates to oral methods for inhibiting bone resorption in a mammal while minimizing the occurrence of or potential for adverse gastrointestinal effects. These methods comprise orally administering to a mammal in need thereof of a pharmaceutically effective amount of a bisphosphonate as a unit dosage according to a continuous schedule having a dosing interval selected from the group consisting of once-weekly dosing, twice-weekly dosing, biweekly dosing, and twice-monthly dosing. The present invention also relates to pharmaceutical compositions and kits useful for carrying out these methods.

BACKGROUND OF THE INVENTION

A variety of disorders in humans and other mammals involve or are associated with abnormal bone resorption. Such disorders include, but are not limited to, osteoporosis, Paget's disease, periprosthetic bone loss or osteolysis, and hypercalcemia of malignancy. The most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Because osteoporosis, as well as other disorders associated with bone loss, are chronic conditions, it is believed that appropriate therapy will generally require chronic treatment.

Multinucleated cells called osteoclasts are responsible for causing bone loss through a process known as bone resorption. It is well known that bisphosphonates are selective inhibitors of osteoclastic bone resorption, making these compounds important therapeutic agents in the treatment or prevention of a variety of generalized or localized bone disorders caused by or associated with abnormal bone resorption. See H. Fleisch, *Bisphosphonates In Bone Disease, From The Laboratory To The Patient,* 2nd Edition, Parthenon Publishing (1995), which is incorporated by reference herein in its entirety.

At present, a great amount of preclinical and clinical data exists for the potent bisphosphonate compound alendronate. Evidence suggests that other bisphosphonates such as risedronate, tiludronate, ibandronate and zolendronate, have many properties in common with alendronate, including high potency as inhibitors of osteoclastic bone resorption. An older bisphosphonate compound, etidronate, also inhibits bone resorption. However, unlike the more potent bisphosphonates, etidronate impairs mineralization at doses used clinically, and may give rise to osteomalacia, a condition resulting in an undesirable decrease in bone mineralization. See Boyce, B. F., Fogelman, I., Ralston, S. et al. (1984) Lancet 1(8381), pp. 821–824 (1984), and Gibbs, C. J., Aaron, J. E.; Peacock, M. (1986) Br. Med. J. 292, pp. 1227-1229 (1986), both of which are incorporated by reference herein in their entirety.

Despite their therapeutic benefits, bisphosphonates are poorly absorbed from the gastrointestinal tract. See B. J. Gertz et al., *Clinical Pharmacology of Alendronate Sodium, Osteoporosis Int.,* Suppl. 3: S13–16 (1993) and B. J. Gertz et al., *Studies of the oral bioavailability of alendronate, Clinical Pharmacology & Therapeutics,* vol. 58, number 3, pp. 288–298 (September 1995), which are incorporated by reference herein in their entirety. Intravenous administration has been used to overcome this bioavailability problem. However, intravenous administration is costly and inconvenient, especially when the patient must be given an intravenous infusion lasting several hours on repeated occasions.

If oral administration of the bisphosphonate is desired, relatively high doses must be administered to compensate for the low bioavailability from the gastrointestinal tract. To offset this low bioavailability, it is generally recommended that the patient take the bisphosphonate on an empty stomach and fast for at least 30 minutes afterwards. However, many patients find the need for such fasting on a daily basis to be inconvenient. Moreover, oral administration has been associated with adverse gastrointestinal effects, especially those relating to the esophagus. See Fleisch, Id. These effects appear to be related to the irritant potential of the bisphosphonate in the esophagus, a problem which is exacerbated by the presence of refluxed gastric acid. For example, the bisphosphonate, pamidronate has been associated with esophageal ulcers. See E. G. Lufkin et al., *Pamidronate: An Unrecognized Problem in Gastrointestinal Tolerability, Osteoporosis International,* 4: 320–322 (1994), which is incorporated by reference herein in its entirety. Although not as common, the use of alendronate has been associated with esophagitis and/or esophageal ulcers. See P. C. De Groen, et al., *Esophagitis Associated With The Use Of Alendronate, New England Journal of Medicine,* vol. 335, no. 124, pp. 1016–1021 (1996), D. O. Castell, *Pill Esophagitis—The Case of Alendronate, New England Journal of Medicine,* vol. 335, no. 124, pp. 1058–1059 (1996), and U. A. Liberman et al., *Esophagitis and Alendronate, New England Journal of Medicine,* vol. 335, no. 124, pp. 1069–1070 (1996), which are incorporated by reference herein in their entirety. The degree of adverse gastrointestinal effects of bisphosphonates has been shown to increase with increasing dose. See C. H. Chestnut et al., *Alendronate Treatment of the Postmenopausal Osteoporotic Woman: Effect of Multiple Dosages on Bone Mass and Bone Remodeling, The American Journal of Medicine,* vol. 99, pp. 144–152, (August 1995), which is incorporated by reference herein in its entirety. Also, these adverse esophageal effects appear to be more prevalent in patients who do not take the bisphosphonate with an adequate amount of liquid or who lie down shortly after dosing, thereby increasing the chance for esophageal reflux.

Current oral bisphosphonate therapies generally fall into two categories: (1) those therapies utilizing continuous daily treatment, and (2) those therapies utilizing a cyclic regimen of treatment and rest periods.

The continuous daily treatment regimens normally involve the chronic administration of relatively low doses of the bisphosphonate compound, with the objective of delivering the desired cumulative therapeutic dose over the course of the treatment period. However, continuous daily dosing has the potential disadvantage of causing adverse gastrointestinal effects due to the repetitive, continuous, and additive irritation to the gastrointestinal tract. Also, because bisphosphonates should be taken on an empty stomach followed by fasting and maintenance of an upright posture for at least 30 minutes, many patients find daily dosing to be burdensome. These factors can therefore interfere with patient compliance, and in severe cases even require cessation of treatment.

Cyclic treatment regimens were developed because some bisphosphonates, such as etidronate, when given daily for more than several days, have the disadvantage of actually causing a decline in bone mineralization, i.e. osteomalacia. U.S. Pat. No. 4,761,406, to Flora et al, issued Aug. 2, 1988, which is incorporated by reference herein in its entirety, describes a cyclic regimen developed in an attempt to minimize the decline in bone mineralization while still providing a therapeutic anti-resorptive effect. Generally, cyclic regimens are characterized as being intermittent, as opposed to continuous treatment regimens, and have both treatment periods during which the bisphosphonate is administered and nontreatment periods to permit the systemic level of the bisphosphonate to return to baseline. However, the cyclic regimens, relative to continuous dosing, appear to result in a decreased therapeutic antiresorptive efficacy. Data on risedronate suggests that cyclic dosing is actually less effective than continuous daily dosing for maximizing antiresorptive bone effects. See L. Mortensen, et al., *Prevention Of Early Postmenopausal Bone Loss By Risedronate, Journal of Bone and Mineral Research*, vol. 10, supp. 1, p. s140 (1995), which is incorporated by reference herein in its entirety. Furthermore, these cyclic regimens do not eliminate or minimize adverse gastrointestinal effects, because such regimens typically utilize periods of multiple daily dosing. Also, the cyclic regimens are cumbersome to administer and have the disadvantage of low patient compliance, and consequently compromised therapeutic efficacy. U.S. Pat. No. 5,366,965, to Strein, issued Nov. 22, 1994, which is incorporated by reference herein in its entirety, attempts to address the problem of adverse gastrointestinal effects by administering a polyphosphonate compound, either orally, subcutaneously, or intravenously, according to an intermittent dosing schedule having both a bone resorption inhibition period and a no-treatment rest period. However, the regimen has the disadvantage of not being continuous and regular, and requires nontreatment periods ranging from 20 to 120 days. PCT Application No. WO 95/30421, to Goodship et al, published Nov. 16, 1995, which is incorporated by reference herein in its entirety, discloses methods for preventing prosthetic loosening and migration using various bisphosphonate compounds. Administration of a once weekly partial dose of the bisphosphonate is disclosed. However, the reference specifically fails to address the issue of adverse gastrointestinal effects or to disclose administration of larger or multiple dosages.

It is seen from current teachings that both daily and cyclic treatment regimens have shortcomings, and that there is a need for development of a dosing regimen to overcome these shortcomings.

In the present invention, it is found that the adverse gastrointestinal effects that can be associated with daily or cyclic dosing regimens can be minimized by administering the bisphosphonate at a relatively high unit dosage according to a continuous schedule having a dosing interval selected from the group consisting of once-weekly dosing, twice-weekly dosing, biweekly dosing, and twice-monthly dosing. In other words, it is found that the administration of a bisphosphonate at a high relative dosage at a low relative dosing frequency causes less adverse gastrointestinal effects, particularly esophageal effects, compared to the administration of a low relative dosage at a high relative dosing frequency. This result is surprising in view of the teachings suggesting that adverse gastrointestinal effects would be expected to increase as a function of increasing bisphosphonate dosage. Such administration methods of the present invention would be especially beneficial in treating patients that have been identified as suffering from or are susceptible to upper gastrointestinal disorders, e.g. gastrointestinal reflux disease (i.e. "GERD"), esophagitis, dyspepsia (i.e. heatburn), ulcers, and other related disorders. In such patients conventional bisphosphonate therapy could potentially exacerbate or induce such upper gastrointestinal disorders.

From a patient lifestyle standpoint, the methods of the present invention would also be more convenient than daily or cyclic dosing regimens. Patients would be subjected less frequently to the inconvenience of having to take the drug on an empty stomach and having to fast for at least 30 minutes after dosing. Also, patients would not need to keep track of a complex dosing regimen. The methods of the present invention are likely to have the advantage of promoting better patient compliance, which in turn can translate into better therapeutic efficacy.

It is an object of the present invention to provide methods for inhibiting bone resorption and the conditions associated therewith.

It is another object of the present invention to provide methods for treating abnormal bone resorption and the conditions associated therewith It is another object of the present invention to provide methods for preventing abnormal bone resorption and the conditions associated therewith.

It is another object of the present invention to provide methods which are oral methods.

It is another object of the present invention to provide such methods in humans.

It is another object of the present invention to provide such methods in patients that have been identified as suffering from or are susceptible to upper gastrointestinal disorders, e.g. gastrointestinal reflux disease (i.e. "GERD"), esophagitis, dyspepsia (i.e. heatburn), ulcers, and other related disorders.

It is another object of the present invention to provide such methods while minimizing the occurrence of or potential for adverse gastronintestinal effects.

It is another object of the present invention to provide such methods comprising a continuous dosing schedule having a dosing interval selected from the group consisting of weekly dosing, twice-weekly dosing, biweekly dosing, and twice-monthly dosing.

It is another object of the present invention to provide such methods comprising a continuous dosing schedule having a dosing periodicity ranging from about once every 3 days to about once every 16 days.

It is another object of the present invention to provide such methods wherein the continuous dosing schedule is maintained until the desired therapeutic effect is achieved.

It is another object of the present invention to treat or prevent abnormal bone resorption in an osteoporotic mammal, preferably an osteoporotic human.

It is another object of the present invention to provide pharmaceutical compositions and kits useful in the methods herein.

These and other objects will become readily apparent from the detailed description which follows.

SUMMARY OF THE INVENTION

The present invention relates to methods for inhibiting bone resorption in a mammal in need thereof, while minimizing the occurrence of or potential for adverse gastrointestinal effects, said method comprising orally administering to said mammal a pharmaceutically effective amount of a bisphosphonate as a unit dosage according to a continuous schedule having a dosing interval selected from the group consisting of once-weekly dosing, twice-weekly dosing, biweekly dosing, and twice-monthly dosing, wherein said continuous schedule is maintained until the desired therapeutic effect is achieved for said mammal.

In other embodiments, the present invention relates to methods comprising a continuous dosing schedule having a dosing periodicity ranging from about once every 3 days to about once every 16 days.

In other embodiments, the present invention relates to methods for treating abnormal bone resorption in a mammal in need of such treatment.

In other embodiments, the present invention relates to methods for preventing abnormal bone resorption in a mammal in need of such prevention.

In other embodiments, the present invention relates to such methods useful in humans.

In other embodiments, the present invention relates to such methods useful in humans identified as having or being susceptible to upper gastrointestinal disorders.

In other embodiments, the present invention relates to methods for treating or preventing osteoporosis in a mammal.

In other embodiments, the present invention relates to methods for treating or preventing osteoporosis in a human.

In other embodiments, the present invention relates to methods for inhibiting bone resorption, or treating or preventing abnormal bone resorption in a human comprising administering to said human from about 8.75 mg to about 140 mg, on an alendronic acid active basis, of a bisphosphonate selected from the group consisting of alendronate, pharmaceutically acceptable salts thereof, and mixtures thereof.

In other embodiments the present invention relates to a pharmaceutical composition comprising from about 8.75 mg to about 140 mg, on an alendronic acid active basis, of a bisphosphonate selected from the group consisting of alendronate, pharmaceutically acceptable salts thereof, and mixtures thereof.

All percentages and ratios used herein, unless otherwise indicated, are by weight. The invention hereof can comprise, consist of, or consist essentially of the essential as well as optional ingredients, components, and methods described herein.

DESCRIPTION OF THE INVENTION

Figure 1:
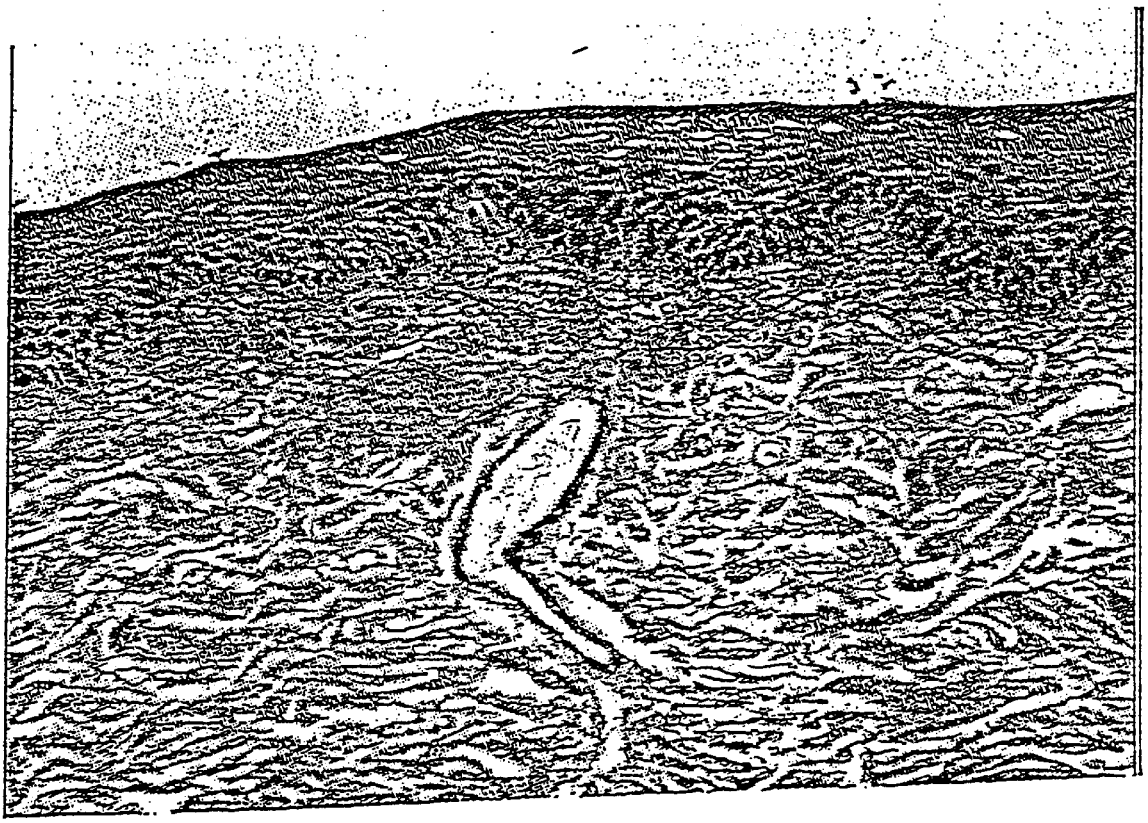
FIG. 1 is a photomicrograph (total magnification 270×) of canine esophagus tissue (paraffin embedded and stained with hematoxylin and eosin) from an animal sacrificed immediately after infusion of the last of five separate dosages of 50 mL of simulated gastric juice administered on five consecutive days.

The present invention relates to a method, preferably an oral method, for inhibiting bone resorption in a mammal in need thereof, while minimizing the occurrence of or potential for adverse gastrointestinal effects. The present invention relates to methods of treating or preventing abnormal bone resorption in a mammal in need of such treatment or prevention. The methods of the present invention comprise orally administering to a mammal a pharmaceutically effective amount of a bisphosphonate as a unit dosage, wherein said dosage is administered according to a continuous schedule having a dosing interval selected from the group consisting of once-weekly dosing, twice-weekly dosing, biweekly dosing, and twice-monthly dosing. In other embodiments, the present invention relates to methods comprising a continuous dosing schedule having a dosing periodicity ranging from about once every 3 days to about once every 16 days. Typically, the continuous dosing schedule is maintained until the desired therapeutic effect is achieved for the mammal.

The present invention utilizes higher unit dosages of the bisphosphonate at each dosing point than has heretofore been typically administered, yet because of the dosing schedule chosen, the potential for adverse gastrointestinal effects are minimized. Moreover, the method is more convenient because the disadvantages associated with daily dosing are minimized.

The methods of the present invention are generally administered to mammals in need of bisphosphonate therapy. Preferably the mammals are human patients, particularly human patients in need of inhibiting bone resorption, such as patients in need of treating or preventing abnormal bone resorption.

The administration methods of the present invention are especially useful in administering bisphosphonate therapy to human patients that have been identified as suffering from or are susceptible to upper gastrointestinal disorders, e.g. GERD, esophagitis, dyspepsia, ulcers, etc. In such patients conventional bisphosphonate therapy could potentially exacerbate or induce such upper gastrointestinal disorders.

The term "pharmaceutically effective amount", as used herein, means that amount of the bisphosphonate compound, that will elicit the desired therapeutic effect or response when administered in accordance with the desired treatment regimen. A preferred pharmaceutically effective amount of the bisphosphonate is a bone resorption inhibiting amount.

The term "minimize the occurrence of or potential for adverse gastrointestinal effects", as used herein, means reducing, preventing, decreasing, or lessening the occurrence of or the potential for incurring unwanted side effects in the gastrointestinal tract, i.e. the esophagus, stomach, intestines, and rectum, particularly the upper gastrointestinal tract, i.e. the esophagus and stomach. Nonlimiting adverse gastrointestinal effects include, but are not limited to GERD, esophagitis, dyspepsia, ulcers, esophageal irritation, esophageal perforation, abdominal pain, and constipation.

The term "abnormal bone resorption", as used herein means a degree of bone resorption that exceeds the degree of bone formation, either locally, or in the skeleton as a whole. Alternatively, "abnormal bone resorption" can be associated with the formation of bone having an abnormal structure.

The term "bone resorption inhibiting", as used herein, means treating or preventing bone resorption by the direct or indirect alteration of osteoclast formation or activity. Inhibition of bone resorption refers to treatment or prevention of bone loss, especially the inhibition of removal of existing bone either from the mineral phase and/or the organic matrix phase, through direct or indirect alteration of osteoclast formation or activity.

The terms "continuous schedule" or "continuous dosing schedule", as used herein, mean that the dosing regimen is repeated until the desired therapeutic effect is achieved. The continuous schedule or continuous dosing schedule is distinguished from cyclical or intermittent administration.

The term "until the desired therapeutic effect is achieved", as used herein, means that the bisphosphonate compound is continuously administered, according to the dosing schedule chosen, up to the time that the clinical or medical effect sought for the disease or condition is observed by the clinician or researcher. For methods of treatment of the present invention, the bisphosphonate compound is continuously administered until the desired change in bone mass or structure is observed. In such instances, achieving an increase in bone mass or a replacement of abnormal bone structure with more normal bone structure are the desired objectives. For methods of prevention of the present invention, the bisphosphonate compound is continuously administered for as long as necessary to prevent the undesired condition. In such instances, maintenance of bone mass density is often the objective. Nonlimiting examples of administration periods can range from about 2 weeks to the remaining lifespan of the mammal. For humans, administration periods can range from about 2 weeks to the remaining lifespan of the human, preferably from about 2 weeks to about 20 years, more preferably from about 1 month to about 20 years, more preferably from about 6 months to about 10 years, and most preferably from about 1 year to about 10 years.

Methods of the Present Invention

The present invention comprises methods for inhibiting bone resorption in mammals. The present invention also comprises treating abnormal bone resorption in mammals. The present invention also comprises methods for preventing abnormal bone resorption in mammals. In preferred embodiments of the present invention, the mammal is a human.

The methods of the present invention do not have the disadvantages of current methods of treatment which can cause or increase the potential for adverse gastrointestinal effects or which require cumbersome, irregular, or complicated dosing regimens.

The present invention comprises a continuous dosing schedule whereby a unit dosage of the bisphosphonate is regularly administered according to a dosing interval selected from the group consisting of once-weekly dosing, twice-weekly dosing, biweekly dosing, and twice-monthly dosing.

By once-weekly dosing is meant that a unit dosage of the bisphosphonate is administered once a week, i.e. one time during a seven day period, preferably on the same day of each week. In the once-weekly dosing regimen, the unit dosage is generally administered about every seven days. A nonlimiting example of a once-weekly dosing regimen would entail the administration of a unit dosage of the bisphosphonate every Sunday. It is preferred that the unit dosage is not administered on consecutive days, but the once-weekly dosing regimen can include a dosing regimen in which unit dosages are administered on two consecutive days falling within two different weekly periods.

By twice-weekly dosing is meant that a unit dosage of the bisphosphonate is administered twice a week, i.e. two times during a seven day period, preferably on the same two days of each weekly period. In the twice-weekly dosing regimen, each unit dosage is generally administered about every three to four days. A nonlimiting example of a twice-weekly dosing regimen would entail the administration of a unit dosage of the bisphosphonate every Sunday and Wednesday. It is preferred that the unit dosages are not administered on the same or consecutive days, but the twice-weekly dosing regimen can include a dosing regimen in which unit dosages are administered on two consecutive days within a weekly period or different weekly periods.

By biweekly dosing is meant that a unit dosage of the bisphosphonate is administered once during a two week period, i.e. one time during a fourteen day period, preferably on the same day during each two week period. In the twice-weekly dosing regimen, each unit dosage is generally administered about every fourteen days. A nonlimiting example of a biweekly dosing regimen would entail the administration of a unit dosage of the bisphosphonate every other Sunday. It is preferred that the unit dosage is not administered on consecutive days, but the biweekly dosing regimen can include a dosing regimen in which the unit dosage is administered on two consecutive days within two different biweekly periods.

By twice-monthly dosing is meant that a unit dosage of the bisphosphonate is administered twice, i.e. two times, during a monthly calendar period. With the twice-monthly regimen, the doses are preferably given on the same two dates of each month. In the twice-monthly dosing regimen, each unit dosage is generally administered about every fourteen to sixteen days. A nonlimiting example of a biweekly dosing regimen would entail dosing on or about the first of the month and on or about the fifteenth, i.e. the midway point, of the month. It is preferred that the unit dosages are not administered on the same or consecutive days but the twice-monthly dosing regimen can include a dosing regimen in which the unit dosages are administered on two consecutive days within a monthly period, or different monthly periods. The twice-monthly regimen is defined herein as being distinct from, and not encompassing, the biweekly dosing regimen because the two regimens have a different periodicity and result in the administration of different numbers of dosages over long periods of time. For example, over a one year period, a total of about twenty four dosages would be administered according to the twice-monthly regimen (because there are twelve calendar months in a year), whereas a total of about twenty six dosages would be administered according to the biweekly dosing regimen (because there are about fifty-two weeks in a year).

In further embodiments or descriptions of the present invention, the unit dosage is given with a periodicity ranging from about once every 3 days to about once every 16 days.

The methods and compositions of the present invention are useful for inhibiting bone resorption and for treating and preventing abnormal bone resorption and conditions associated therewith. Such conditions include both generalized and localized bone loss. Also, the creation of bone having an abnormal structure, as in Paget's disease, can be associated with abnormal bone resorption. The term "generalized bone loss" means bone loss at multiple skeletal sites or throughout the skeletal system. The term "localized bone loss" means bone loss at one or more specific, defined skeletal sites.

Generalized boss loss is often associated with osteoporosis. Osteoporosis is most common in post-menopausal women, wherein estrogen production has been greatly diminished. However, osteoporosis can also be steroid-induced and has been observed in males due to age. Osteoporosis can be induced by disease, e.g. rheumatoid arthritis, it can be induced by secondary causes, e.g., glucocorticoid therapy, or it can come about with no identifiable cause, i.e. idiopathic osteoporosis. In the present invention, preferred methods include the treatment or prevention of abnormal bone resorption in osteoporotic humans.

Localized bone loss has been associated with periodontal disease, with bone fractures, and with periprosthetic osteolysis (in other words where bone resorption has occurred in proximity to a prosthetic implant).

Generalized or localized bone loss can occur from disuse, which is often a problem for those confined to a bed or a wheelchair, or for those who have an immobilized limb set in a cast or in traction.

The methods and compositions of the present invention are useful for treating and or preventing the following conditions or disease states: osteoporosis, which can include post-menopausal osteoporosis, steroid-induced osteoporosis, male osteoporosis, disease-induced osteoporosis, idiopathic osteoporosis; Paget's disease; abnormally increased bone turnover; periodontal disease; localized bone loss associated with periprosthetic osteolysis; and bone fractures.

The methods of the present invention are intended to specifically exclude methods for the treatment and/or prevention of prosthesis loosening and prosthesis migration in mammals as described in PCT application WO 95/30421, to Goodship et al, published Nov. 16, 1995, which is incorporated by reference herein in its entirety.

Bisphosphonates

The methods and compositions of the present invention comprise a bisphosphonate. The bisphosphonates of the present invention correspond to the chemical formula

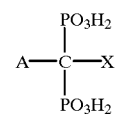

wherein
A and X are independently selected from the group consisting of H, OH, halogen, $NH_2$, SH, phenyl, C1–C30 alkyl, C1–C30 substituted alkyl, C1–C10 alkyl or dialkyl substituted $NH_2$, C1–C10 alkoxy, C1–C10 alkyl or phenyl substituted thio, C1–C10 alkyl substituted phenyl, pyridyl, furanyl, pyrrolidinyl, imidazonyl, and benzyl.

In the foregoing chemical formula, the alkyl groups can be straight, branched, or cyclic, provided sufficient atoms are selected for the chemical formula. The C1–C30 substituted alkyl can include a wide variety of substituents, nonlimiting examples which include those selected from the group consisting of phenyl, pyridyl, furanyl, pyrrolidinyl, imidazonyl, $NH_2$, C1–C10 alkyl or dialkyl substituted $NH_2$, OH, SH, and C1–C10 alkoxy.

In the foregoing chemical formula, A can include X and X can include A such that the two moieties can form part of the same cyclic structure.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Preferred structures are those in which A is selected from the group consisting of H, OH, and halogen, and X is selected from the group consisting of C1–C30 alkyl, C1–C30 substituted alkyl, halogen, and C1–C10 alkyl or phenyl substituted thio.

More preferred structures are those in which A is selected from the group consisting of H, OH, and Cl, and X is selected from the group consisting of C1–C30 alkyl, C1–C30 substituted alkyl, Cl, and chlorophenylthio.

Most preferred is when A is OH and X is a 3-aminopropyl moiety, so that the resulting compound is a 4-amino-1,-hydroxybutylidene-1,1-bisphosphonate, i.e. alendronate.

Pharmaceutically acceptable salts and derivatives of the bisphosphonates are also useful herein. Nonlimiting examples of salts include those selected from the group consisting alkali metal, alkaline metal, ammonium, and mono-, di, tri-, or tetra-C1–C30-alkyl-substituted ammonium. Preferred salts are those selected from the group consisting of sodium, potassium, calcium, magnesium, and ammonium salts. Nonlimiting examples of derivatives include those selected from the group consisting of esters, hydrates, and amides.

"Pharmaceutically acceptable" as used herein means that the salts and derivatives of the bisphosphonates have the same general pharmacological properties as the free acid form from which they are derived and are acceptable from a toxicity viewpoint.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those or ordinary skill in the art, reference to a specific weight or percentage of a bisphosphonate compound in the present invention is on an acid active weight basis, unless indicated otherwise herein. For example, the phrase "about 70 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 70 mg of alendronic acid.

Nonlimiting examples of bisphosphonates useful herein include the following:

Alendronic acid, 4-amino-1-hydroxybutylidene-1,1-bisphosphonic acid.

Alendronate (also known as alendronate sodium or monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990, and U.S. Pat. No. 5,019,651, to Kieczykowski, issued May 28, 1991, both of which are incorporated by reference herein in their entirety.

Cycloheptylaminomethylene-1,1-bisphosphonic acid, YM 175, Yamanouchi (cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and $J$ $Org.$ $Chem$ 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zolendronate).

Preferred are bisphosphonates selected from the group consisting of alendronate, cimadronate, clodronate, tiludronate, etidronate, ibandronate, risedronate, piridronate, pamidronate, zolendronate, pharmaceutically acceptable salts thereof, and mixtures thereof.

More preferred is alendronate, pharmaceutically acceptable salts thereof, and mixtures thereof.

Most preferred is alendronate monosodium trihydrate.

Pharmaceutical Compositions

Compositions useful in the present invention comprise a pharmaceutically effective amount of a bisphosphonate. The bisphosphonate is typically administered in admixture with suitable pharmaceutical diluents, excipients, or carriers, collectively referred to herein as "carrier materials", suitably selected with respect to oral administration, i.e. tablets, capsules, elixirs, syrups, effervescent compositions, powders, and the like, and consistent with conventional pharmaceutical practices. For example, for oral administration in the form of a tablet, capsule, or powder, the active ingredient can be combined with an oral, non-toxic, pharmaceutically acceptable inert carrier such as lactose, starch, sucrose, glucose, methyl cellulose, magnesium stearate, mannitol, sorbitol, croscarmellose sodium and the like; for oral administration in liquid form, e.g., elixirs and syrups, effervescent compositions, the oral drug components can be combined with any oral, non-toxic, pharmaceutically acceptable inert carrier such as ethanol, glycerol, water and the like. Moreover, when desired or necessary, suitable binders, lubricants, disintegrating agents, buffers, coatings, and coloring agents can also be incorporated. Suitable binders can include starch, gelatin, natural sugars such a glucose, anhydrous lactose, free-flow lactose, beta-lactose, and corn sweeteners, natural and synthetic gums, such as acacia, guar, tragacanth or sodium alginate, carboxymethyl cellulose, polyethylene glycol, waxes, and the like. Lubricants used in these dosage forms include sodium oleate, sodium stearate, magnesium stearate, sodium benzoate, sodium acetate, sodium chloride and the like. A particularly preferred tablet formulation for alendronate monosodium trihydrate is that described in U.S. Pat. No. 5,358,941, to Bechard et al, issued Oct. 25, 1994, which is incorporated by reference herein in its entirety. The compounds used in the present method can also be coupled with soluble polymers as targetable drug carriers. Such polymers can include polyvinylpyrrolidone, pyran copolymer, polyhydroxylpropylmethacrylamide, and the like.

The precise dosage of the bisphonate will vary with the dosing schedule, the oral potency of the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 $\mu$g/kg body weight and preferably about 10 to about 2000 $\mu$g/kg of body weight.

For human oral compositions comprising alendronate, pharmaceutically acceptable salts thereof, or pharmaceutically acceptable derivatives thereof, a unit dosage typically comprises from about 8.75 mg to about 140 mg of the alendronate compound, on an alendronic acid active weight basis.

For once-weekly dosing, an oral unit dosage comprises from about 17.5 mg to about 70 mg of the alendronate compound, on an alendronic acid active weight basis. Examples of weekly oral dosages include a unit dosage which is useful for osteoporosis prevention comprising about 35 mg of the alendronate compound, and a unit dosage which is useful for treating osteoporosis comprising about 70 mg of the alendronate compound.

For twice-weekly dosing, an oral unit dosage comprises from about 8.75 mg to about 35 mg of the alendronate compound, on an alendronic acid active weight basis. Examples of twice-weekly oral dosages include a unit dosage which is useful for osteoporosis prevention comprising about 17.5 mg of the alendronate compound, and a unit dosage which is useful for osteoporosis treatment, comprising about 35 mg of the alendronate compound.

For biweekly or twice-monthly dosing, an oral unit dosage comprises from about 35 mg to about 140 mg of the alendronate compound, on an alendronic acid active weight basis. Examples of biweekly or twice-monthly oral dosages include a unit dosage which is useful for osteoporosis prevention comprising about 70 mg of the alendronate compound, and a unit dosage which is useful for osteoporosis treatment, comprising about 140 mg of the alendronate compound.

Nonlimiting examples of oral compositions comprising alendronate, as well as other bisphosphonates, are illustrated in the Examples, below.

Sequential Administration of Histamine H2 Receptor Blockers and/or Proton Pump Inhibitors With Bisphosphonates In further embodiments, the methods and compositions of the present invention can also comprise a histamine H2 receptor blocker (i.e. antagonist) and/or a proton pump inhibitor. Histamine H2 receptor blockers and proton pump inhibitors are well known therapeutic agents for increasing gastric pH. See L. J. Hixson, et al., *Current Trends in the Pharmacotherapy for Peptic Ulcer Disease*, Arch. Intern. Med., vol. 152, pp. 726–732 (April 1992), which is incorporated by reference herein in its entirety. It is found in the present invention that the sequential oral administration of a histamine H2 receptor blocker and/or a proton pump inhibitor, followed by a bisphosphonate can help to further minimize adverse gastrointestinal effects. In these embodiments, the histamine H2 receptor blocker and/or proton pump inhibitor is administered from about 30 minutes to about 24 hours prior to the administration of the bisphosphonate. In more preferred embodiments, the histamine H2 receptor blocker and/or proton pump inhibitor is administered from about 30 minutes to about 12 hours prior to the administration of the bisphonate.

The dosage of the histamine H2 receptor blocker and/or proton pump inhibitor will depend upon the particular compound selected and factors associated with the mammal to be treated, i.e. size, health, etc.

Nonlimiting examples of histamine H2 receptor blockers and/or proton pump inhibitors include those selected from the group consisting of cimetidine, famotidine, nizatidine, ranitidine, omeprazole, and lansoprazole.

Treatment Kits

In further embodiments, the present invention relates to a kit for conveniently and effectively carrying out the methods in accordance with the present invention. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered. Alternatively, placebo dosages, or calcium or dietary supplements, either in a form similar to or distinct from the bisphosphonate dosages, can be included to provide a kit in which a dosage is taken every day. In those embodiments including a histamine H2 receptor and/or proton pump inhibitor, these agents can be included as part of the kit.

EXAMPLES

The following examples further describe and demonstrate embodiments within the scope of the present invention. The examples are given solely for the purpose of illustration and are not to be construed as limitations of the present invention as many variations thereof are possible without departing from the spirit and scope of the invention.

Example 1

Esophageal Irritation Potential

The esophageal irritation potential of the bisphosphonates is evaluated using a dog model.

The experiments demonstrate the relative irritation potential of the following dosing regimens: placebo (Group 1), a single high concentration dosage of alendronate monosodium trihydrate (Group 2), a low concentration dosage of alendronate monosodium trihydrate administered for five consecutive days (Groups 3 and 4), a high concentration dosage of alendronate monosodium trihydrate administered once per week for four weeks (Group 5), a mid-range concentration dosage of alendronate monosodium trihydrate administered twice per week for four weeks (Group 6), a low dosage of risedronate sodium administered for five consecutive days (Group 7), and a low dosage of tiludronate disodium administered for five consecutive days (Group 8).

The following solutions are prepared:

(1) simulated gastric juice (pH about 2), i.e. the control solution.

(2) simulated gastric juice (pH about 2) containing about 0.20 mg/mL of alendronate monosodium trihydrate on an alendronic acid active basis.

(3) simulated gastric juice (pH about 2) containing about 0.80 mg/mL of alendronate monosodium trihydrate on an alendronic acid active basis.

(4) simulated gastric juice (pH about 2) containing about 0.40 mg/mL of alendronate monosodium trihydrate on an alendronic acid active basis.

(5) simulated gastric juice (pH about 2) containing about 0.20 mg/mL of risedronate sodium on a risedronic acid active basis.

(6) simulated gastric juice (pH about 2) containing about 4.0 mg/mL of tiludronate disodium on a tiludronic acid active basis.

The simulated gastric juice is prepared by dissolving about 960 mg of pepsin (L-585,228000B003, Fisher Chemical) in about 147 mL of 0.90 (wt %) NaCl (aqueous), adding about 3 mL of 1.0 M HCl (aqueous), and adjusting the volume to about 300 mL with deionized water. The pH of the resulting solution is measured and if necessary is adjusted to about 2 using 1.0 M HCl (aqueous) or 1.0 M NaOH (aqueous).

The animals used in the experiments are anesthetized and administered about 50 mL of the appropriate solution over about 30 minutes by infusion into the esophagus using an infusion pump and a rubber catheter. The following treatment experiments are run:

Group 1: This control group contains four animals. Each animal is administered a dosage of about 50 mL of simulated gastric juice [solution (1)] on each of five consecutive days. The animals are sacrificed immediately after the last dose is administered.

Group 2: This group contains four animals. Each animal is administered a dosage of about 50 mL of simulated gastric juice containing about 0.20 mg/mL of alendronate [solution (2)] on each of five consecutive days. The animals are sacrificed immediately after the last dose is administered.

Group 3: This group contains five animals. Each animal is administered a dosage of about 50 mL of simulated gastric juice containing about 0.80 mg/mL of alendronate [solution (3)] on a single treatment day. The animals are sacrificed about 24 hours after the dose is administered.

Group 4: This group contains five animals. Each animal is administered a dosage of about 50 mL of simulated gastric juice containing about 0.80 mg/mL of alendronate [solution (3)] on a single treatment day. The animals are sacrificed about 7 days after the dose is administered.

Group 5: This group contains six animals. Each animal is administered a dosage of about 50 mL of simulated gastric juice containing about 0.80 mg/mL of alendronate [solution (3)] once per week, i.e. every seven days, for four weeks. The animals are administered a total of four dosages. The animals are sacrificed about 7 days after the last dose is administered.

Group 6: This group contains six animals. Each animal is administered a dosage of about 50 mL of simulated gastric juice containing about 0.40 mg/mL of alendronate [solution (4)] twice per week, i.e. every three to four days, for four weeks. The animals are administered a total of eight dosages. The animals are sacrificed about four days after the last dose is administered.

Group 7: This group contains eight animals. Each animal is administered a dosage of about 50 mL of simulated gastric juice containing about 0.20 mg/mL of risedronate [solution (5)] on each of five consecutive days. The animals are sacrificed immediately after the last dose is administered.

Group 8: This group contains four animals. Each animal is administered a dosage of about 50 mL of simulated gastric juice containing about 4.0 mg/mL of tiludronate [solution (6)] on each of five consecutive days. The animals are sacrificed immediately after the last dose is administered.

The esophagus from each sacrificed animal is removed and prepared for histopathology using standard techniques by embedding the tissue in paraffin, staining with hematoxylin and eosin. The sections are examined microscopically. The histopathology results are summarized in Table 1.

For the Group 1 animals (control group), the photomicrographs show that the esophagus is normal with an intact epithelium and absence of inflammatory cells in the submucosa. FIG. 1 is a representative photomicrograph from a Group 1 animal.

Figure 2:
FIG. 2 is a photomicrograph (total magnification 270×) of canine esophagus tissue (paraffin embedded and stained with hematoxylin and eosin) from an animal sacrificed immediately after infusion of the last of five separate dosages of 50 mL of 0.20 mg/mL alendronate in simulated gastric juice administered on five consecutive days.

For the Group 2 animals, the photomicrographs show that the esophagus exhibits deep ulceration of the epithelial surface and marked submucosal inflammation and vacuolation. FIG. 2 is a representative photomicrograph from a Group 2 animal.

Figure 3:
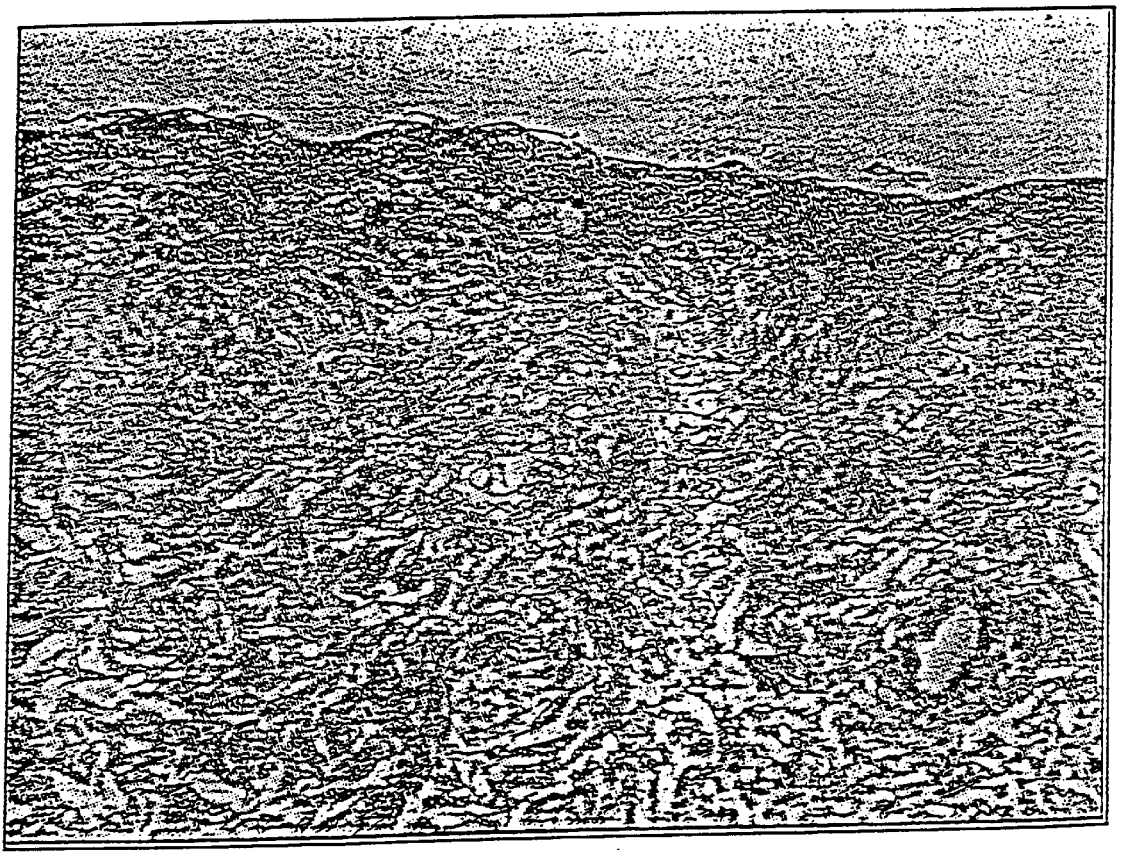
FIG. 3 is a photomicrograph (total magnification 270×) of canine esophagus tissue (paraffin embedded and stained with hematoxylin and eosin) from an animal sacrificed 24 hours after infusion with a single dosage of 50 mL of 0.80 mg/mL alendronate in simulated gastric juice.

For the Group 3 animals, the photomicrographs show that the esophagus has an intact epithelial surface with very slight submucosal inflammation and vacuolation. FIG. 3 is a representative photomicrograph from a Group 3 animal.

Figure 4:
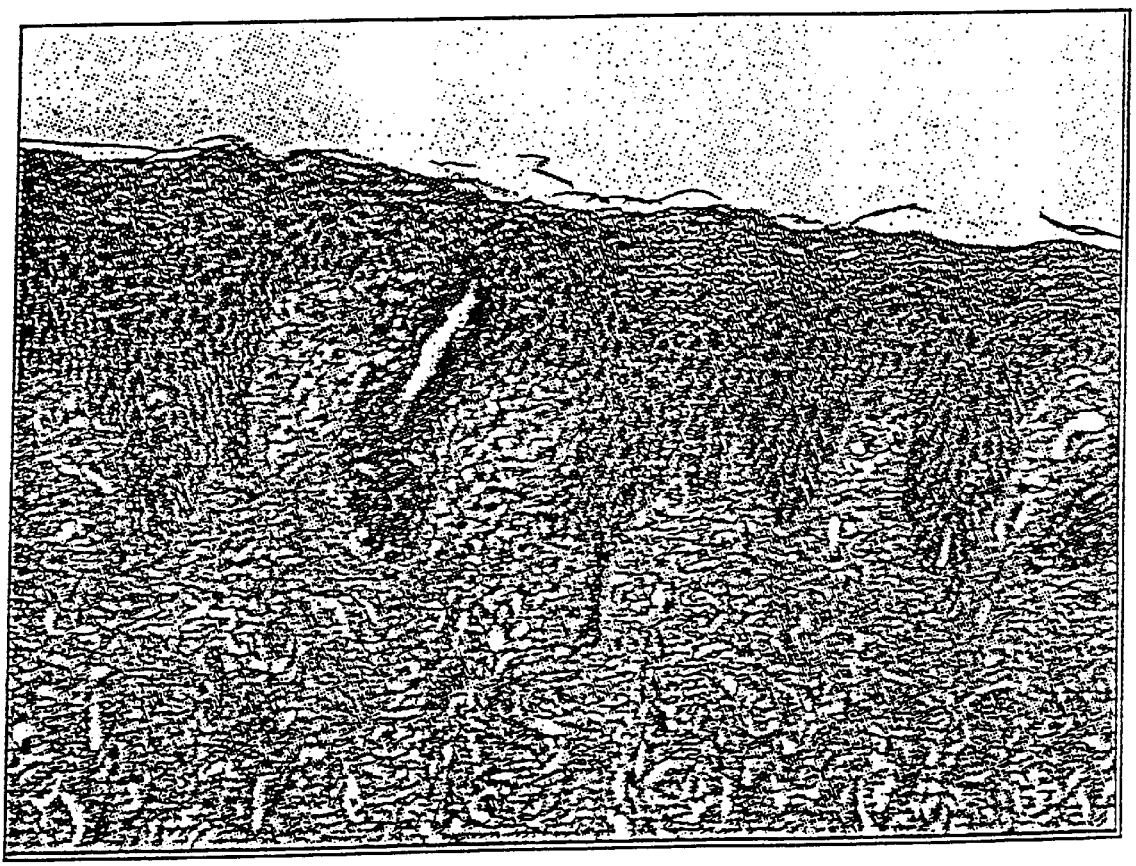
FIG. 4 is a photomicrograph (total magnification 270×) of canine esophagus tissue (paraffin embedded and stained with hematoxylin and eosin) from an animal sacrificed 7 days after infusion with a single dosage of 50 mL of 0.80 mg/mL alendronate in simulated gastric juice.

For the Group 4 animals, the photomicrographs show that the esophagus has an intact epithelium with either minimal inflammation (two of the five animals) or no inflammation (three of the five animals) and no vacuolation. FIG. 4 is a representative photomicrograph from a Group 4 animal exhibiting minimal inflammation.

Figure 5:
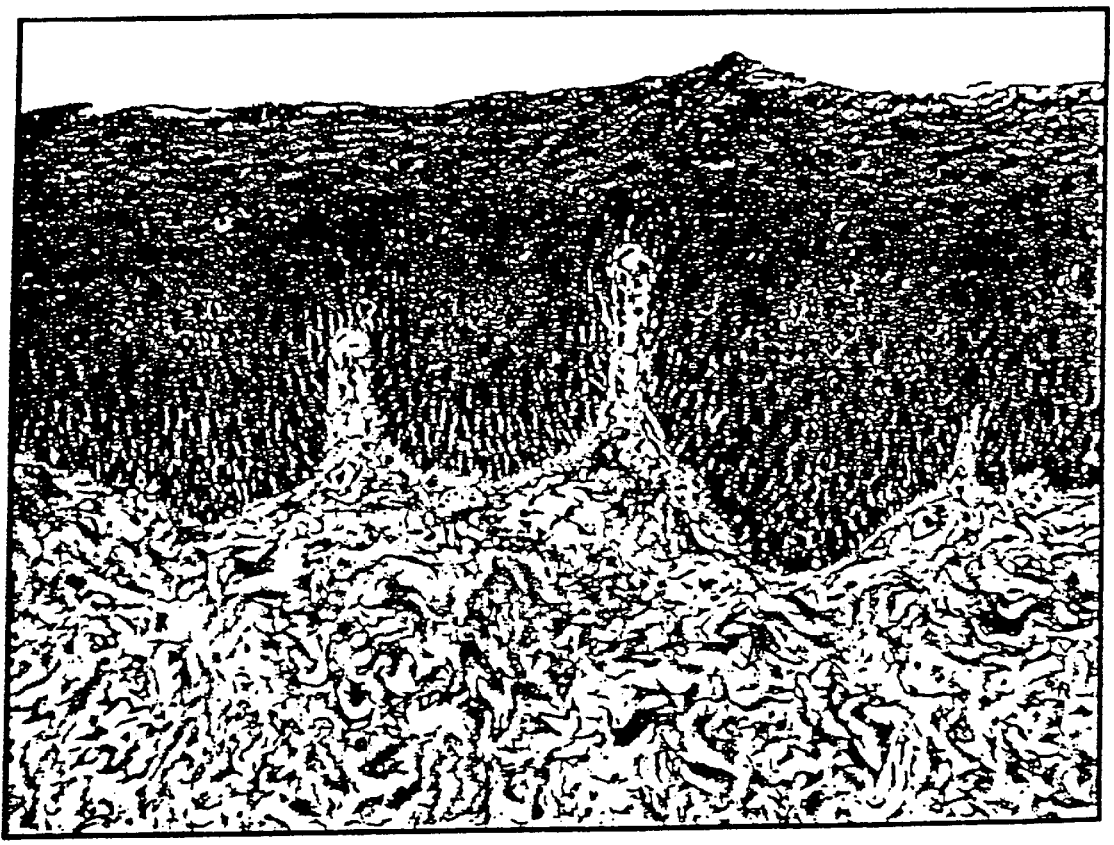
FIG. 5 is a photomicrograph (total magnification 270×) of canine esophagus tissue (paraffin embedded and stained with hematoxylin and eosin) from an animal sacrified 7 days after infusion of the last of 4 separate dosages of 50 mL of 0.80 mg/mL alendronate in simulated gastric juice administered once per week, i.e. once every 7 days.

For the Group 5 animals, the photomicrographs show that the esophagus is normal with an intact epithelium and absence of inflammatory cells in the submucosa. FIG. 5 is a representative photomicrograph from a Group 5 animal.

Figure 6:
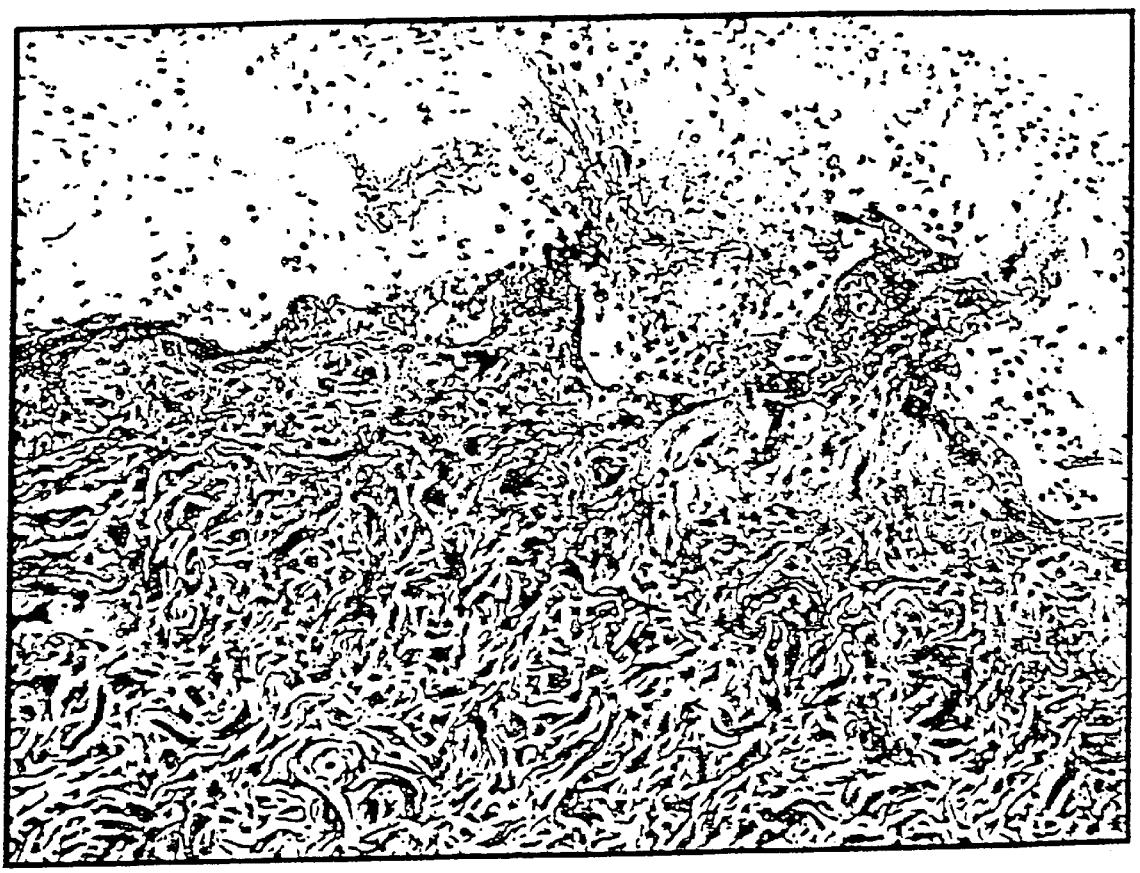
FIG. 6 is a photomicrograph (total magnification 270×) of canine esophagus tissue (paraffin embedded and stained with hematoxylin and eosin) from an animal sacrified 4 days after infusion of the last of 8 separate dosages of 50 mL of 0.40 mg/mL alendronate in simulated gastric juice administered twice per week, i.e. once every 3–4 days.

For the Group 6 animals, the photomicrographs show that the esophagus exhibits deep ulceration of the epithelial surface and marked submucosal inflammation and vacuolation. FIG. 6 is a representative photomicrograph from a Group 6 animal.

Figure 7:
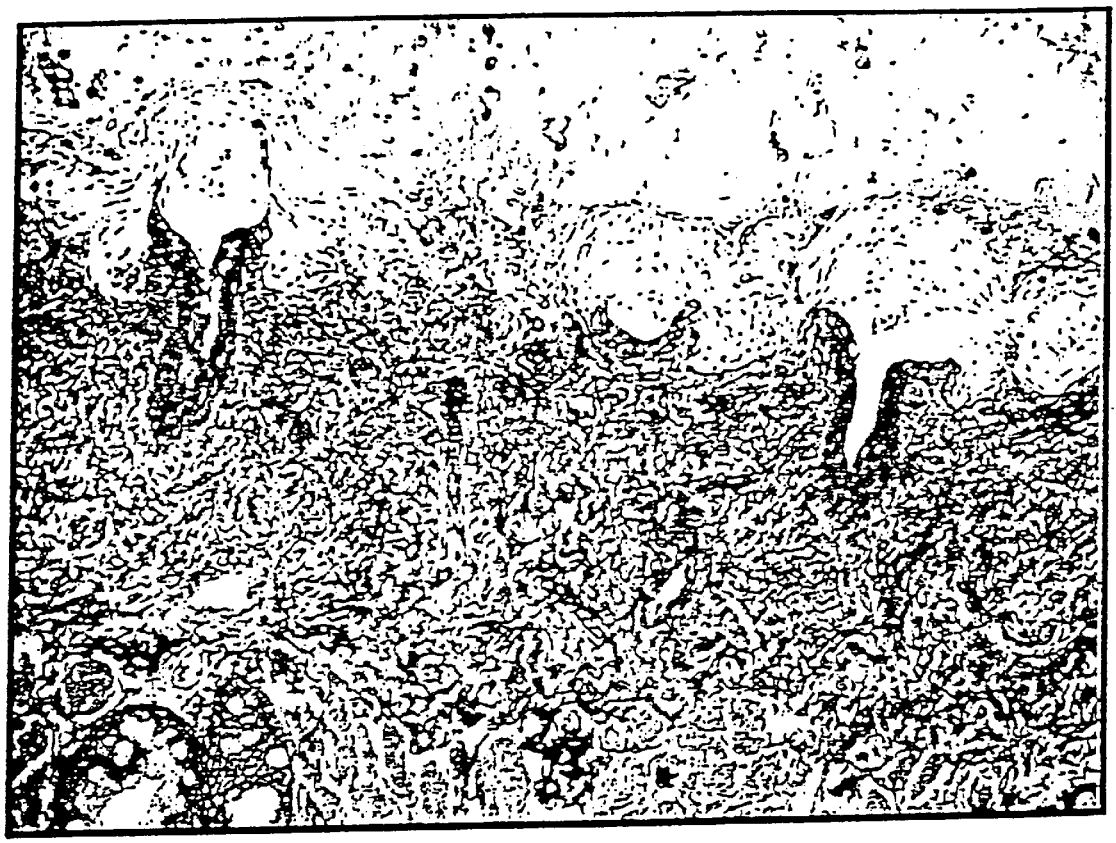
FIG. 7 is a photomicrograph (total magnification 270×) of canine esophagus tissue (paraffin embedded and stained with hematoxylin and eosin) from an animal sacrificed immediately after infusion of the last of five separate dosages of 50 mL of 0.20 mg/mL risedronate in simulated gastric juice administered on five consecutive days.

For the Group 7 animals, the photomicrographs show that the esophagus exhibits deep ulceration of the epithelial surface and marked submucosal inflammation and vacuolation. FIG. 7 is a representative photomicrograph from a Group 7 animal.

Figure 8:
FIG. 8 is a photomicrograph (total magnification 270×) of canine esophagus tissue (paraffin embedded and stained with hematoxylin and eosin) from an animal sacrificed immediately after infusion of the last of five separate dosages of 50 mL of 4.0 mg/mL tiludronate in simulated gastric juice administered on five consecutive days.

For the Group 8 animals, the photomicrographs show that the esophagus exhibits slight ulceration of the epithelial surface and slight submucosal inflammation and vacuolation. FIG. 8 is a representative photomicrograph from a Group 8 animal.

These experiments demonstrate that considerably less esophageal irritation (comparable to control Group 1)is observed from the administration of a single high concentration dosage of alendronate (Groups 3 and 4) versus administration of low concentration dosages on consecutive days (Group 2). These experiments also demonstrate consideraly less esophageal irritation is observed from the administration of a single high concentration of alendronate on a weekly basis (Group 5) or twice-weekly basis (Group 6) versus administration of low concentration dosages on consecutive days (Group 2). These experiments also demonstrate that when other bisphosphonates such as risedronate (Group 7) or tiludronate (Group 8) are administered at low dosages on consecutive days that the esophageal irritation potential is high.

TABLE 1

Esophageal Irritation Potential Studies

| Group | Active Agent mg/mL | Dosing Schedule | Sacrifice Time | Histo-pathology |
|---|---|---|---|---|
| 1 (n = 4) | 0 | 1X daily for 5 days | immediately after last dosing | Normal. Intact epithelium and absence of inflammatory cells in the submucosa. |
| 2 | Alendronate | 1X daily | immediately | Deep ulceration of |

TABLE 1-continued

Esophageal Irritation Potential Studies

| Group | Active Agent mg/mL | Dosing Schedule | Sacrifice Time | Histo-pathology |
|---|---|---|---|---|
| (n = 4) | 0.20 | for 5 days | after last dosing | epithelial surface. Marked submucosal inflammation and vacuolation. |
| 3 (n = 5) | Alendronate 0.80 | 1X | 24 hours after dosing | Intact epithelial surface with very slight submucosal inflammation and vacuolation. |
| 4 (n = 5) | Alendronate 0.80 | 1X | 7 days after dosing | Intact epithelium with either minimal inflammation (2 of 5 animals) or no inflammation (3 of 5 animals) and no vacuolation. |
| 5 (n = 6) | Alendronate 0.80 | 1X weekly for a total of 4 doses | 7 days after last dosing | Intact epithelium with no inflammation and no vacuolation. |
| 6 (n = 6) | Alendronate 0.40 | 2X weekly for 4 weeks | immediately after last dosing | Deep ulceration of epithelial surface. Marked submucosal inflammation and vacuolation. |
| 7 (n = 8) | Risedronate 0.20 | 1X daily for 5 days | immediately after last dosing | Deep ulceration of epithelial surface (4 of 8 animals). Marked submucosal inflammation and vacuolation. |
| 8 (n = 4) | Tiludronate 4.0 | 1X daily for 5 days | 24 hours after last dosing | Slight submucosal inflammation and vacuolation (3 of 4 animals, including 1 of these animals with slight ulceration). |

Example 2

Once-weekly dosing regimen
Treatment of osteoporosis

Alendronate tablets or liquid formulations containing about 70 mg of alendronate, on an alendronic acid active basis, are prepared (see EXAMPLES 7 and 8). The tablets or liquid formulations are orally administered to a human patient once-weekly, i.e. preferably about once every seven days (for example, every Sunday), for a period of at least one year. This method of administration is useful and convenient for treating osteoporosis and for minimizing adverse gastrointestinal effects, particularly adverse esophageal effects. This method is also useful for improving patient acceptance and compliance.

Prevention of Osteoporosis

Alendronate tablets or liquid formulations containing about 35 mg of alendronate, on an alendronic acid active basis, are prepared (see EXAMPLES 7 and8). The tablets or liquid formulations are orally administered to a human patient once-weekly, i.e. preferably about once every seven days (for example, every Sunday), for a period of at least one year. This method of administration is useful and convenient for preventing osteoporosis and for minimizing adverse gastrointestinal effects, particularly adverse esophageal effects. This method is also useful for improving patient acceptance and compliance.

Example 3

Twice-weekly Dosing Regimen
Treatment of Osteoporosis

Alendronate tablets or liquid formulations containing about 35 mg of alendronate, on an alendronic acid active basis, are prepared (see EXAMPLES 7 and 8). The tablets or liquid formulations are orally administered to a human patient twice-weekly, preferably about once every three or four days (for example, every Sunday and Wednesday), for a period of at least one year. This method of administration is useful and convenient for treating osteoporosis and for minimizing adverse gastrointestinal effects, particularly adverse esophageal effects. This method is also useful for improving patient acceptance and compliance.

Prevention of Osteoporosis

Alendronate tablets or liquid formulations containing about 17.5 mg of alendronate, on an alendronic acid active basis, are prepared (see EXAMPLES 7 and8). The tablets or liquid formulations are orally administered to a human patient twice-weekly, preferably about once every three or four days (for example, every Sunday and Wednesday), for a period of at least one year. This method of administration is useful and convenient for preventing osteoporosis and for minimizing adverse gastrointestinal effects, particularly adverse esophageal effects. This method is also useful for improving patient acceptance and compliance.

Example 4

Biweekly Dosing Regimen
Treatment of Osteoporosis

Alendronate tablets or liquid formulations containing about 140 mg of alendronate, on an alendronic acid active basis, are prepared (see EXAMPLES 7 and 8). The tablets or liquid formulations are orally administered to a human patient biweekly, i.e. preferably about once every fourteen days (for example, on alternate Sundays), for a period of at least one year. This method of administration is useful and convenient for treating osteoporosis and for minimizing adverse gastrointestinal effects, particularly adverse esophageal effects. This method is also useful for improving patient acceptance and compliance.

Prevention of Osteoporosis

Alendronate tablets or liquid formulations containing about 70 mg of alendronate, on an alendronic acid active basis, are prepared (see EXAMPLES 7 and 8). The tablets or liquid formulations are orally administered to a human patient biweekly, i.e. preferably about once every fourteen days (for example, on alternate Sundays), for a period of at least one year. This method of administration is useful and convenient for preventing osteoporosis and for minimizing adverse gastrointestinal effects, particularly adverse esophageal effects. This method is also useful for improving patient acceptance and compliance.

Example 5

Twice-monthly Dosing Regimen
Treatment of Osteoporosis

Alendronate tablets or liquid formulations containing about 140 mg of alendronate, on an alendronic acid active basis, are prepared (see EXAMPLES 7 and 8). The tablets or liquid formulations are orally administered to a human twice-monthly, i.e. preferably about once every fourteen to sixteen days (for example, on about the first and fifteenth of each month), for a period of at least one year. This method of administration is useful and convenient for treating osteoporosis and for minimizing adverse gastrointestinal effects, particularly adverse esophageal effects. This method is also useful for improving patient acceptance and compliance.

Prevention of Osteoporosis

Alendronate tablets or liquid formulations containing about 70 mg of alendronate, on an alendronic acid active basis, are prepared (see EXAMPLES 7 and 8). The tablets or liquid formulations are orally administered to a human patient biweekly, i.e. preferably once every fourteen to sixteen days (for example, on about the first and fifteenth of each month), for a period of at least one year. This method of administration is useful and convenient for preventing osteoporosis and for minimizing adverse gastrointestinal effects, particularly adverse esophageal effects. This method is also useful for improving patient acceptance and compliance.

Example 6

In further embodiments, alendronate tablets or liquid formulations are orally dosed, at the desired dosage, according to the dosing schedules of EXAMPLES 2–5, for treating or preventing other disorders associated with abnormal bone resorption.

In yet further embodiments, other bisphosphonate compounds are orally dosed, at the desired dosage, according to the dosing schedules of EXAMPLES 2–5, for treating or preventing osteoporosis or for treating or preventing other conditions associated with abnormal bone resorption.

Example 7

Bisphosphonate Tablets

Bisphosphonate containing tablets are prepared using standard mixing and formation techniques as described in U.S. Pat. No. 5,358,941, to Bechard et al., issued Oct. 25, 1994, which is incorporated by reference herein in its entirety.

Tablets containing about 35 mg of alendronate, on an alendronic acid active basis, are prepared using the following relative weights of ingredients.

| Ingredient | Per Tablet | Per 4000 Tablets |
| --- | --- | --- |
| Alendronate Monosodium Trihydrate | 45.68 mg | 182.72 g |
| Anhydrous Lactose, NF | 71.32 mg | 285.28 g |
| Microcrystalline Cellulose, NF | 80.0 mg | 320.0 g |
| Magnesium Stearate, NF | 1.0 mg | 4.0 g |
| Croscarmellose Sodium, NF | 2.0 mg | 8.0 g |

The resulting tablets are useful for administration in accordance with the methods of the present invention for inhibiting bone resorption.

Similarly, tablets comprising other relative weights of alendronate, on an alendronic acid active basis are prepared: e.g., about 8.75, 17.5, 70, and 140 mg per tablet. Also, tablets containing other bisphosphonates at appropriate active levels are similarly prepared: e.g., cimadronate, clodronate, tiludronate, etidronate, ibandronate, risedronate, piridronate, pamidronate, zolendronate, and pharmaceutically acceptable salts thereof. Also, tablets containing combinations of bisphosphonates are similarly prepared.

Example 8

Liquid Bisphosphonate Formulation

Liquid bisphosphonate formulations are prepared using standard mixing techniques.

A liquid formulation containing about 70 mg of alendronate monosodium trihydrate, on an alendronic acid active basis, per about 75 mL of liquid is prepared using the following relative weights of ingredients.

| Ingredient | Weight |
| --- | --- |
| Alendronate Monosodium Trihydrate | 91.35 mg |
| Sodium Propylparaben | 22.5 mg |
| Sodium Butylparaben | 7.5 mg |
| Sodium Citrate Dihydrate | 1500 mg |
| Citric Acid Anhydrous | 56.25 mg |
| Sodium Saccharin | 7.5 mg |
| Water | qs 75 mL |
| 1 N Sodium Hydroxide (aq) | qs pH 6.75 |

The resulting liquid formulation is useful for administration as a unit dosage in accordance with the methods of the present invention for inhibiting bone resorption.

Similarly, liquid formulations comprising other relative weights of alendronate, on an alendronic acid active basis, per unit dosage are prepared: e.g., about 8.75, 17.5, 35, and 140 mg per 75 mL volume. Also, the liquid formulations are prepared to provide other volumes for the unit dosage, e.g. about 135 mL. Also, the liquid formulations are prepared containing other bisphosphonates at appropriate active levels: e.g., cimadronate, clodronate, tiludronate, etidronate, ibandronate, risedronate, piridronate, pamidronate, zolendronate, and pharmaceutically acceptable salts thereof. Also, liquid formulations containing combinations of bisphosphonates are similarly prepared.

What is claimed is:

1. A method for inhibiting bone resorption in a mammal, in need thereof, comprising sequentially orally administering to said mammal, in need thereof a pharmaceutically effective amount of a unit dosage of a histamine H2 receptor blocker or a proton pump inhibitor and a unit dosage of a bisphosphonate according to a continuous schedule having a dosing interval selected from the group consisting of once-weekly dosing, twice-weekly dosing, biweekly dosing, and twice-monthly dosing.

2. A method according to claim 1 wherein said histamine H2 blocker or said proton pump inhibitor is administered from about 30 minutes to about 24 hours prior to the administration of said bisphosphonate.

3. A method according to claim 2 wherein said bisphosphonate is selected from the group consisting of alendronate, cimadronate, clodronate, tiludronate, etidronate, ibandronate, risedronate, piridronate, pamidronate, zoledronate, pharmaceutically acceptable salts or esters thereof, and mixtures thereof.

4. A method according to claim 3 wherein said bisphosphonate is selected from the group consisting of alendronate, pharmaceutically acceptable salts or esters thereof, and mixtures thereof.

5. A method according to claim 4 wherein said pharmaceutically acceptable salt is alendronate monosodium trihydrate.

6. A method according to claim 3 wherein said bisphosphonate is selected from the group consisting of risedronate, pharmaceutically acceptable salts or esters thereof, and mixtures thereof.

7. A method according to claim 5 wherein said mammal is a human.

8. A method according to claim 7 wherein said dosing interval is once-weekly.

9. A method according to claim 8 wherein said unit dosage of said bisphosphonate comprises from about 17.5 mg to about 70 mg of alendronate monosodium trihydrate, on an alendronic acid active basis.

10. A method according to claim 9 wherein said unit dosage of said bisphosphonate comprises about 70 mg of alendronate monosodium trihydrate, on an alendronic acid active basis.

11. A method according to claim 7 wherein said dosing interval is twice-weekly.

12. A method according to claim 11 wherein said unit dosage of said bisphosphonate comprises from about 8.75 mg to about 35 mg of alendronate monosodium trihydrate, on an alendronic acid active basis.

13. A method according to claim 7 wherein said dosing interval is biweekly.

14. A method according to claim 13 wherein said unit dosage of said bisphosphonate comprises from about 35 mg to about 140 mg of alendronate monosodium trihydrate, on an alendronic acid active basis.

15. A method according to claim 7 wherein said dosing interval is twice-monthly.

16. A method according to claim 15 wherein said unit dosage of said bisphosphonate comprises about 35 mg to about 140 mg of alendronate monosodium trihydrate, on an alendronic acid active basis.

17. A method for treating osteoporosis in a mammal in need thereof comprising sequentially orally administering to said mammal a pharmaceutically effective amount of a unit dosage of a histamine H2 receptor blocker or a proton pump inhibitor and a unit dosage of a bisphosphonate according to a continuous schedule having a dosing interval selected from the group consisting of once-weekly dosing, twice-weekly dosing, biweekly dosing, and twice-monthly dosing.

18. A method according to claim 17 wherein said histamine H2 blocker or said proton pump inhibitor is administered from about 30 minutes to about 24 hours prior to the administration of said bisphosphonate.

19. A method according to claim 18 wherein said bisphosphonate is selected from the group consisting of alendronate, cimadronate, clodronate, tiludronate, etidronate, ibandronate, risedronate, piridronate, pamidronate, zoledronate, pharmaceutically acceptable salts or esters thereof, and mixtures thereof.

20. A method according to claim 19 wherein said bisphosphonate is selected from the group consisting of alendronate, pharmaceutically acceptable salts or esters thereof, and mixtures thereof.

21. A method according to claim 20 wherein said pharmaceutically acceptable salt is alendronate monosodium trihydrate.

22. A method according to claim 19 wherein said bisphosphonate is selected from the group consisting of risedronate, pharmaceutically acceptable salts or esters thereof, and mixtures thereof.

23. A method according to claim 21 wherein said mammal is a human.

24. A method according to claim 23 wherein said dosing interval is once-weekly.

25. A method according to claim 24 wherein said unit dosage of said bisphosphonate comprises about 70 mg of alendronate monosodium trihydrate, on an alendronic acid active basis.

26. A method according to claim 23 wherein said dosing interval is twice-weekly.

27. A method according to claim 26 wherein said unit dosage of said bisphosphonate comprises about 35 mg of alendronate monosodium trihydrate, on an alendronic acid active basis.

28. A method according to claim 23 wherein said dosing interval is biweekly.

29. A method according to claim 27 wherein said unit dosage of said bisphosphonate comprises about 140 mg of alendronate monosodium trihydrate, on an alendronic acid active basis.

30. A method according to claim 23 wherein said dosing interval is twice-monthly.

31. A method according to claim 30 wherein said unit dosage of said bisphosphonate comprises about 140 mg of alendronate monosodium trihydrate, on an alendronic acid active basis.

32. A method for preventing osteoporosis in a mammal, in need thereof, comprising sequentially orally administering to said mammal, in need thereof a pharmaceutically effective amount of a unit dosage of a histamine H2 receptor blocker or a proton pump inhibitor and a unit dosage of a bisphosphonate according to a continuous schedule having a dosing interval selected from the group consisting of once-weekly dosing, twice-weekly dosing, biweekly dosing, and twice-monthly dosing.

33. A method according to claim 32 wherein said histamine H2 receptor blocker or said proton pump inhibitor is administered from about 30 minutes to about 24 hours prior to the administration of said bisphosphonate.

34. A method according to claim 33 wherein said bisphosphonate is selected from the group consisting of alendronate, cimadronate, clodronate, tiludronate, etidronate, ibandronate, risedronate, piridronate, pamidronate, zoledronate, pharmaceutically acceptable salts or esters thereof, and mixtures thereof.

35. A method according to claim 34 wherein said bisphosphonate is selected from the group consisting of alendronate, pharmaceutically acceptable salts or esters thereof, and mixtures thereof.

36. A method according to claim 35 wherein said pharmaceutically acceptable salt is alendronate monosodium trihydrate.

37. A method according to claim 34 wherein said bisphosphonate is selected from the group consisting of risedronate, pharmaceutically acceptable salts or esters thereof, and mixtures thereof.

38. A method according to claim 36 wherein said mammal is a human.

39. A method according to claim 38 wherein said dosing interval is once-weekly.

40. A method according to claim 39 wherein said bisphosphonate unit dosage comprises about 35 mg of alendronate monosodium trihydrate, on an alendronic acid active basis.

41. A method according to claim 38 wherein said dosing interval is twice-weekly.

42. A method according to claim 41 wherein said bisphosphonate unit dosage comprises about 17.5 mg of alendronate monosodium trihydrate, on an alendronic acid active basis.

43. A method according to claim 38 wherein said dosing interval is biweekly.

44. A method according to claim 38 wherein said bisphosphonate unit dosage comprises about 70 mg of alendronate monosodium trihydrate, on an alendronic acid active basis.

45. A method according to claim 38 wherein said dosing interval is twice-monthly.

46. A method according to claim 45 wherein said bisphosphonate unit dosage comprises about 70 mg of alendronate monosodium trihydrate, on an alendronic acid active basis.

47. A method according to any of claims 1–46 wherein said histamine H2 receptor blocker or proton pump inhibitor is selected from the group consisting of cimetidine, famotidine, nizatidine, ranitidine, omeprazole, and lansoprazole.

48. A kit comprising, comprising:
   (a) at least one pharmaceutically effective unit dosage of a bisphosphonate for oral administration, and
   (b) at least one pharmaceutically effective unit dosage of a histamine H2 receptor blocker or a proton pump inhibitor.

49. A kit according to claim 48 wherein said bisphosphonate is selected from the group consisting of alendronate, cimadronate, clodronate, tiludronate, etidronate, ibandronate, risedronate, piridronate, pamidronate, zoledronate, pharmaceutically acceptable salts or esters thereof, and mixtures thereof.

50. A kit according to claim 49 wherein said bisphosphonate is selected from the group consisting of alendronate, pharmaceutically acceptable salts or esters thereof, and mixtures thereof.

51. A kit according to claim 50 wherein said pharmaceutically acceptable salt is alendronate monosodium trihydrate.

52. A kit according to claim 51 wherein said histamine H2 receptor blocker or proton pump inhibitor is selected from the group consisting of cimetidine, famotidine, nizatidine, ranitidine, omeprazole, and lansoprazole.

53. A kit according to claim 49 wherein said bisphosphonate is selected from the group consisting of risedronate, pharmaceutically acceptable salts or esters thereof, and mixtures thereof.

54. A kit according to claim 53 wherein said histamine H2 receptor blocker or proton pump inhibitor is selected from the group consisting of cimetidine, famotidine, nizatidine, ranitidine, omeprazole, and lansoprazole.

55. A kit according to any of claims 48–54 wherein said unit dosage of said bisphosphonate comprises from about 1.5 to about 6000 µg/kg body weight.

56. A kit according to claim 55 wherein said unit dosage of said bisphosphonate comprises from about 10 to about 2000 µg/kg body weight.

57. A kit according to claim 50 wherein said unit dosage comprises from about 8.75 to about 140 mg of said bisphosphonate on an alendronic acid active basis.

58. A kit according to claim 57 wherein said unit dosage comprises about 35 mg of said bisphosphonate on an alendronic acid active basis.

59. A kit according to claim 57 wherein said unit dosage comprises about 70 mg of said bisphosphonate on an alendronic acid active basis.

60. A kit according to claim 51 wherein said unit dosage comprises from about 8.75 to about 140 mg of said bisphosphonate on an alendronic acid active basis.

61. A kit according to claim 60 wherein said unit dosage comprises about 35 mg of said bisphosphonate on an alendronic acid active basis.

62. A kit according to claim 60 wherein said unit dosage comprises about 70 mg of said bisphosphonate on an alendronic acid active basis.

63. A kit according to claim 52 wherein said unit dosage comprises from about 8.75 to about 140 mg of said bisphosphonate on an alendronic acid active basis.

64. A kit according to claim 63 wherein said unit dosage comprises about 35 mg of said bisphosphonate on an alendronic acid active basis.

65. A kit according to claim 63 wherein said unit dosage comprises about 70 mg of said bisphosphonate on an alendronic acid active basis.

* * * * *